(12) United States Patent
Oura et al.

(10) Patent No.: US 9,783,773 B2
(45) Date of Patent: Oct. 10, 2017

(54) CELL CULTURE APPARATUS

(75) Inventors: Mitsuhiro Oura, Tokyo (JP); Teruo Okano, Tokyo (JP); Tatsuya Shimizu, Tokyo (JP); Hirotsugu Kubo, Tokyo (JP); Sunao Takeda, Tokyo (JP)

(73) Assignees: NIHON KOHDEN CORPORATION, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 809 days.

(21) Appl. No.: 13/432,658

(22) Filed: Mar. 28, 2012

(65) Prior Publication Data

US 2012/0252110 A1   Oct. 4, 2012

(30) Foreign Application Priority Data

Mar. 28, 2011 (JP) ................................. 2011-070259

(51) Int. Cl.
  *C12M 1/32* (2006.01)
  *C12M 1/00* (2006.01)
(52) U.S. Cl.
  CPC ............ *C12M 33/06* (2013.01); *C12M 29/26* (2013.01); *C12M 41/14* (2013.01)
(58) Field of Classification Search
  USPC .......................................... 435/283.1–309.4
  See application file for complete search history.

(56) References Cited

U.S. PATENT DOCUMENTS

| 2002/0155487 A1* | 10/2002 | Greenberger et al. ............ 435/6 |
| 2003/0092178 A1 | 5/2003 | Yerden |
| 2003/0235866 A1* | 12/2003 | Roback et al. ................ 435/7.1 |
| 2010/0291663 A1 | 11/2010 | Koshiba |

FOREIGN PATENT DOCUMENTS

| JP | 2009-180594 A | 8/2009 |
| JP | 4365783 B2 | 8/2009 |
| WO | 2007/120619 A2 | 10/2007 |

OTHER PUBLICATIONS

Extended European Search Report for related European Patent Application No. 12161366.5 dated Jun. 14, 2012.

* cited by examiner

*Primary Examiner* — Nathan Bowers
*Assistant Examiner* — Lydia Edwards
(74) *Attorney, Agent, or Firm* — Kenealy Vaidya LLP

(57) ABSTRACT

A cell culture apparatus includes: an isolator in which a sterile space accommodating a cell incubator filled with a culture solution containing cells to be cultured is disposed; a sampling unit configured to sample the culture solution in the cell incubator; a delivery flow path through which an inside of the sterile space and an outside of the sterile space communicate with each other, the delivery flow path configured to limit a flow in the delivery flow path to a direction that is directed from the inside of the sterile space toward the outside of the sterile space; and a culture solution delivering section configured to deliver the sampled culture solution to the outside of the sterile space via the delivery flow path.

11 Claims, 5 Drawing Sheets

CELL CULTURE APPARATUS

BACKGROUND OF THE INVENTION

The present invention relates to a cell culture apparatus, and more particularly to a cell culture apparatus provided with an isolator including a sterile space for accommodating cell incubators filled with a culture solution containing cells to be cultured is disposed.

In fields such as regenerative medicine and artificial insemination, various related-art culture apparatuses and sampling apparatuses which can be used in cell culture or sampling have been proposed (for example, see Japanese Patent No. 4,365,783 and JP-A-2009-180594). As a type of such apparatuses, also a culture apparatus of the isolator type has been proposed which can accommodate a plurality of cell incubators in an incubator that is maintained in a sterile condition.

In such a culture apparatus of the isolator type, in order to maintain a sterile space in a sterile condition, the sterile space must be highly isolated from the outside. In the case where, for example, a culture solution in a cell incubator is to be sampled, therefore, the cell incubator in the incubator must be once carried out into a pass box or the like which is disposed adjacently to the incubator constituting a sterile space, and then taken out to the outside, with the result that the sampling operation requires much labor and time.

SUMMARY

According to the invention, there is provided a cell culture apparatus comprising: an isolator in which a sterile space accommodating a cell incubator filled with a culture solution containing cells to be cultured is disposed; a sampling unit configured to sample the culture solution in the cell incubator; a delivery flow path through which an inside of the sterile space and an outside of the sterile space communicate with each other, the delivery flow path configured to limit a flow in the delivery flow path to a direction that is directed from the inside of the sterile space toward the outside of the sterile space; and a culture solution delivering section configured to deliver the sampled culture solution to the outside of the sterile space via the delivery flow path.

The delivery flow path may include a one-way valve which does not interrupt a flow directed from the inside of the sterile space toward the outside of the sterile space and which interrupts a flow directed from the outside of the sterile space toward the inside of the sterile space.

The culture solution delivering section may include a buffer substance supplier configured to supply a buffer substance that is used when the sampled culture solution is delivered to the outside of the sterile space.

The buffer substance supplier may be disposed inside the sterile space, and be connected to an end portion of the delivery flow path on a side of the inside of the sterile space.

The buffer substance supplier may be disposed outside the sterile space, and be connected to the sterile space while maintaining a sterile condition.

The culture solution delivering section may include a suction pump configured to suck the culture solution that is sampled by the sampling unit, toward a portion of the delivery flow path on a side of the outside of the sterile space.

The suction pump is a peristalic pump which is disposed in the delivery flow path on a side of one of the inside and the outside of the sterile space.

The suction pump is a negative pressure pump which is connected to an end portion of the delivery flow path on a side of the outside.

The delivery flow path may include an ejection section which is disposed inside the sterile space. The sampling unit may be configured to suck a predetermined amount of the culture solution in the cell incubator and to eject the sucked culture solution into the ejection section.

The cell culture apparatus may further include a measuring device configured to perform measurement on the culture solution which is delivered to the outside of the sterile space via the delivery flow path.

The cell culture apparatus may further include a calibration flow path which is connected to the buffer substance supplier while maintaining a sterile condition, and through which the inside of the sterile space and outside of the sterile space communicate with each other. The measuring device may be configured to perform measurement on the buffer substance which is delivered to the outside of the sterile space via the calibration flow path.

The above description does not list all the necessary features of the invention, but sub-combinations of a group of these features can also constitute the invention.

DETAILED DESCRIPTION OF EMBODIMENTS

Hereinafter, the invention will be described by way of an embodiment thereof. However, the following embodiment is not intended to limit the invention as defined in the appended claims, and all combinations features described in the embodiment are not always essential to solving means of the invention.

Figure 1:
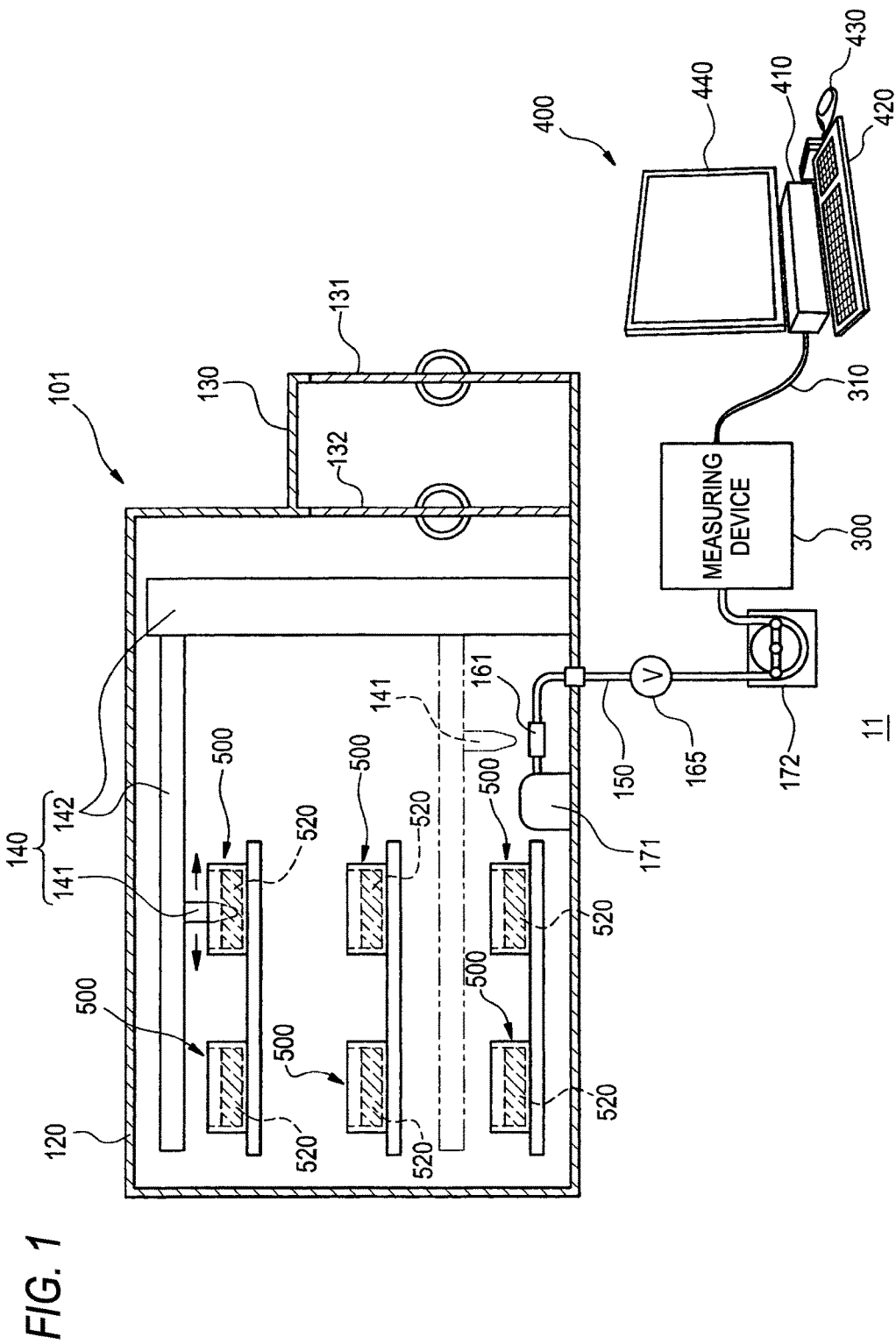
FIG. 1 is a schematic diagram of a cell culture apparatus 11 of an embodiment of the invention.

FIG. 1 is a schematic diagram of a cell culture apparatus 11 of the embodiment of the invention. The cell culture apparatus 11 includes an isolator 101, a measuring device 300, and a data management device 400.

The isolator 101 has a sterile chamber 120 and a pass box 130. The internal space of the sterile chamber 120 is formed as a sterile space which is maintained at a sterility level that is suitable for accommodating cell incubators 500 filled with a culture solution 520 containing cells to be cultured. The internal space is separated from the adjacent pass box 130 so as to be openable and closable via an openable and closable door 132. The pass box 130 is separated from the internal space of the sterile chamber 120 by the openable and closable door 132 as described above, and also from the external space (non-sterile space) by an openable and closable door 131.

In the internal space of the sterile chamber 120, a plurality of (in this example, six) cell incubators 500 filled with the culture solution 520 are accommodated, and a sampling unit 140 which samples the culture solutions 520 in the cell incubators 500 is disposed. The sampling unit 140 includes an injection port 141 which can suck and eject the culture solution 520 in each cell incubator 500 that is to be sampled, and a transport device 142 which transports the injection port 141.

The internal space of the sterile chamber 120 communicates with the outside via a delivery flow path 150. In the case where the interior of the sterile chamber 120 is to be sterilized by a medical agent, a material which is very low reactive with the medical agent is used as the material of the delivery flow path 150.

An end portion of the delivery flow path 150 on the side of the internal space of the sterile chamber 120 is connected to a buffer substance supplier 171 which is disposed inside the sterile space (in the sterile chamber 120) in order to supply a buffer substance to the delivery flow path 150. In the vicinity of the end portion of the delivery flow path 150 in the internal space, an ejection section 161 in which the upper side is opened is disposed. On the other hand, the end portion of the delivery flow path 150 on the side of the external space is connected to the measuring device 300. In a portion of the delivery flow path 150 on the side of the external space, a one-way valve 165 and a peristalic pump 172 are disposed sequentially starting from the side which is closer to the sterile chamber 120. The peristalic pump which is used in the embodiment is one mode of implementation. The pump is not restricted to this, and may be a pump of any type as far as it can suck the culture solution 520 from the ejection section 161.

The one-way valve 165 is a check valve which, in the case where a fluid tries to flow in the delivery flow path 150 from the internal space of the sterile chamber 120 toward the external space, does not interrupt the flow, and which interrupts only the reverse flow (the flow directed from the external space toward the internal space of the sterile chamber 120). The peristalic pump 172 causes the flow from the inner side of the sterile chamber 120 through the delivery flow path 150 to further flow toward the measuring device 300.

The data management device 400 is configured by a device main unit 410, a keyboard 420, a mouse 430, and a display 440. The device main unit 410 is connected to the measuring device 300 via a communication cable 310, and receives various measurement results from the measuring device 300. Moreover, the device main unit 410 displays information such as the measurement results supplied from the measuring device 300, and setting information of the measuring device 300, on the display 440, receives instruction inputs such as a change of the settings through the keyboard 420 or the mouse 430, and outputs the instructions to the measuring device 300.

Hereinafter, a method of sampling the culture solution 520 in one of the cell incubators 500 accommodated in the sterile chamber 120 by using the above-described cell culture apparatus 11 will be specifically described.

First, the buffer substance is continuously flown from the buffer substance supplier 171 to the delivery flow path 150. As the buffer substance which is supplied from the buffer substance supplier 171, for example, a liquid such as sterilized pure water, or a sterilized gas is preferably used. As a result, the state is attained where the delivery flow path 150 is filled with the buffer substance, and the buffer substance is continuously flown from the buffer substance supplier 171 toward the measuring device 300. Next, the injection port 141 is transported by the transport device 142 to the cell incubator 500 which is to be subjected to sampling, and the culture solution 520 in the cell incubator 500 is sucked by the injection port 141.

Then, the injection port 141 in which the sucking operation has been completed is transported to a location immediately above the ejection section 161 by the transport device 142. In the location, the injection port 141 ejects the sucked culture solution 520 toward the ejection section 161. The culture solution 520 which is ejected to the ejection section 161 (hereinafter, such a solution is referred to as "sampling culture solution") is sent to the outside of the sterile chamber 120 by the buffer substance which is continuously flown in the delivery flow path 150. Then, the sampling culture solution is supplied to the measuring device 300 via the one-way valve 165 and the peristalic pump 172, to be subjected to the measurement process.

The measurement items to be performed by the measuring device 300 are not particularly limited, but for example the pH, concentration of carbon dioxide, and glucose content of the sampling culture solution may be measured. In addition to or in place of these measurement items, the measuring device 300 may measure the contents of various constituent elements of the sampling culture solution. Then, the measuring device 300 outputs results of the measurements of the sampling culture solution to the data management device 400. The data management device 400 applies various processes to the measurement results of the sampling culture solution supplied from the measuring device 300, and then displays and stores result data.

As described above, the cell culture apparatus 11 of the embodiment can continuously perform sampling and measurement on the culture solution 520 in the one of the cell incubators 500 which are accommodated in the sterile chamber 120, without, for example, taking out the cell incubator 500 to the outside of the sterile chamber 120 via the pass box 130. Therefore, the labor and time required in sampling can be remarkably reduced.

In the delivery flow path 150, as described above, the one-way valve 165 which does not interrupt the flow directed from the sterile chamber 120 toward the external space, and which interrupts that directed from the external space toward the sterile chamber 120 is disposed, and the peristalic pump 172 which sends the fluid in the delivery flow path 150 in the vicinity of the measuring device 300 to the measuring device 300 is disposed. Therefore, the fluid in the delivery flow path 150 is stably flown from the sterile chamber 120 toward the external space, and there is no possibility that the interior of the sterile chamber 120 is contaminated by the reverse flow.

Figure 2:
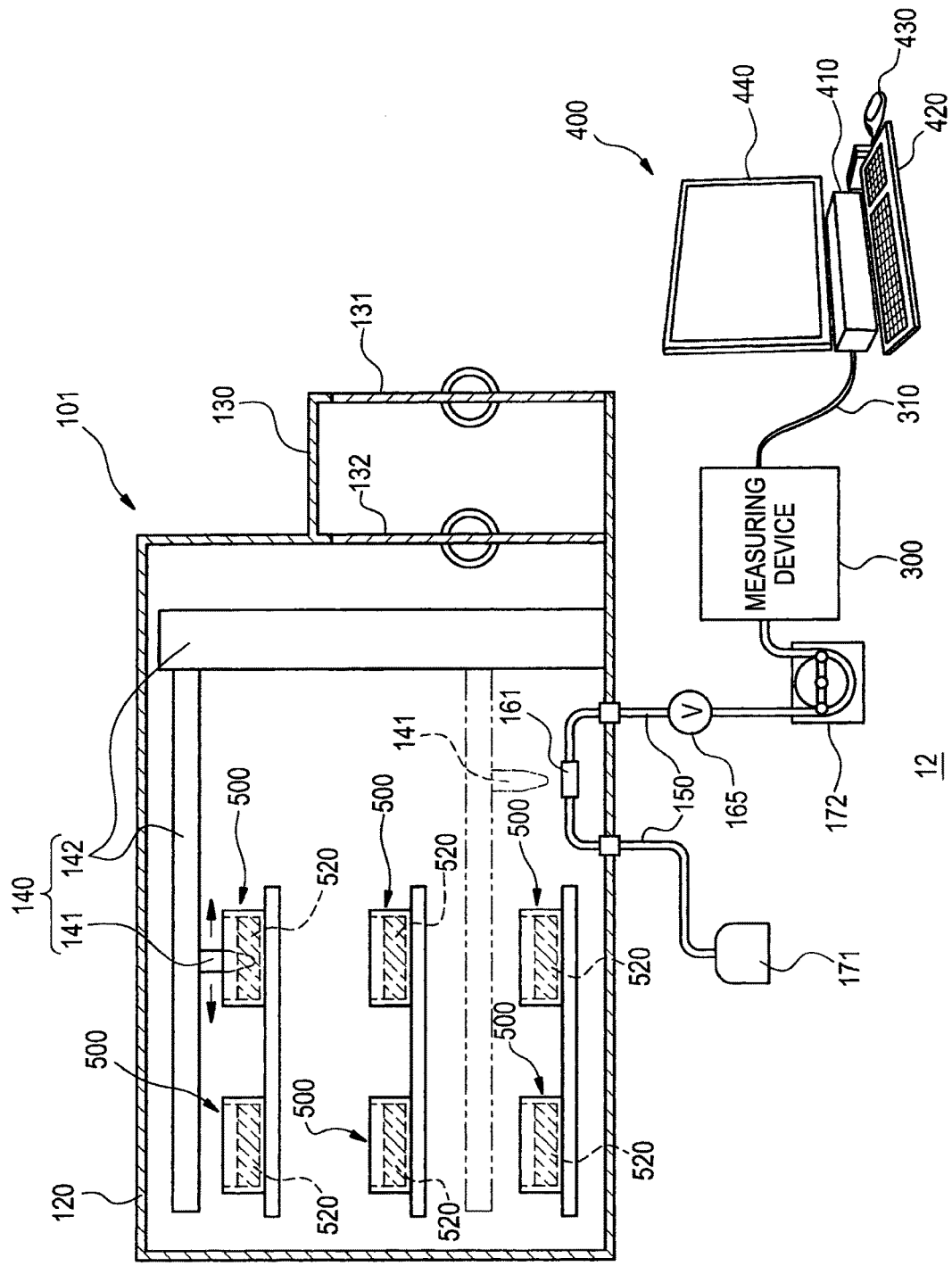
FIG. 2 is a schematic diagram of a cell culture apparatus 12 of another example of the embodiment of the invention.

FIG. 2 is a schematic diagram of a cell culture apparatus 12 of another example of the embodiment of the invention. In the cell culture apparatus 12 that will be described with reference to FIG. 2, components which are identical with those of the cell culture apparatus 11 that has been described with reference to FIG. 1 are denoted by the same reference numerals, and their description is omitted.

In the cell culture apparatus 12 of the example, the buffer substance supplier 171 is disposed outside the sterile space (outside the sterile chamber 120), and connected to one end of the delivery flow path 150. In the example, although the buffer substance supplier 171 is disposed outside the sterile chamber 120, the buffer substance supplier 171 is connected to the sterile space (the interior of the sterile chamber 120) while maintaining the sterile condition. Namely, a tank which stores the buffer substance in the buffer substance supplier 171 is a highly hermetically sealed container the interior of which is maintained to a sterile condition, and connected to the ejection section 161 in the sterile chamber 120 via the delivery flow path 150 the interior of which is similarly maintained to a sterile condition. In the delivery flow path 150, the portion which is on the side of the measuring device 300 with respect to the ejection section 161 is configured in the same manner as the above-described cell culture apparatus 11.

Therefore, the buffer substance which is supplied from the buffer substance supplier 171 that is outside the sterile chamber 120, to the delivery flow path 150 is flown to the measuring device 300 that is outside the sterile chamber 120, via the ejection section 161 in the sterile chamber 120. According to the configuration, in the cell culture apparatus 12, as compared with the case where the buffer substance supplier 171 is disposed in the sterile chamber 120, the supply of the buffer substance to the buffer substance supplier 171 can be performed outside the sterile chamber 120 in a more easily manner.

Figure 3:
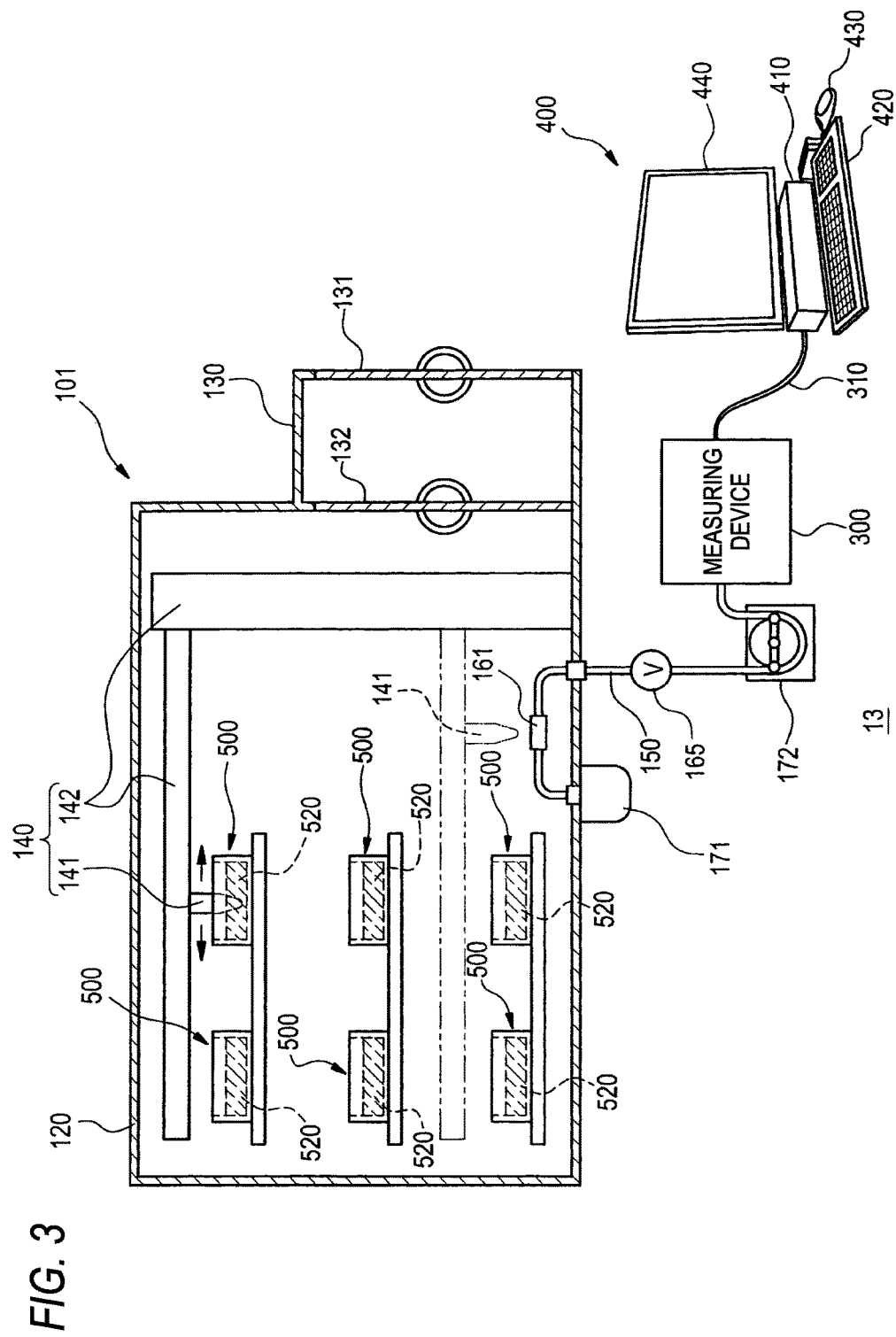
FIG. 3 is a schematic diagram of a cell culture apparatus 13 of a further example of the embodiment of the invention.

FIG. 3 is a schematic diagram of a cell culture apparatus 13 of a further example of the embodiment of the invention. In the cell culture apparatus 13 that will be described with reference to FIG. 3, components which are identical with those of the cell culture apparatus 11 that has been described with reference to FIG. 1, and the cell culture apparatus 12 that has been described with reference to FIG. 2 are denoted by the same reference numerals, and their description is omitted.

In the cell culture apparatus 13 of the example, similarly with the above-described cell culture apparatus 12, the buffer substance supplier 171 is disposed outside the sterile space (outside the sterile chamber 120), and connected to one end of the delivery flow path 150. Similarly with the cell culture apparatus 12, the tank which stores the buffer substance in the buffer substance supplier 171 is a highly hermetically sealed container the interior of which is maintained to a sterile condition, and connected to the ejection section 161 in the sterile chamber 120 via the delivery flow path 150 the interior of which is similarly maintained to a sterile condition. In the delivery flow path 150, the portion which is on the side of the measuring device 300 with respect to the ejection section 161 is configured in the same manner as the above-described cell culture apparatuses 11, 12.

Therefore, the buffer substance which is supplied from the buffer substance supplier 171 that is outside the sterile chamber 120, to the delivery flow path 150 is flown to the measuring device 300 that is outside the sterile chamber 120, via the ejection section 161 in the sterile chamber 120. In the cell culture apparatus 13 of the example, unlike the above-described cell culture apparatus 12, the buffer substance supplier 171 is attached on the wall face of the sterile chamber 120.

According to the configuration, in the cell culture apparatus 13, similarly with the above-described cell culture apparatus 12, the supply of the buffer substance to the buffer substance supplier 171 can be easily performed outside the sterile chamber 120, and the delivery flow path 150 which extends from the buffer substance supplier 171 to the ejection section 161 can be further shortened. This is advantageous also in space saving.

Figure 4:
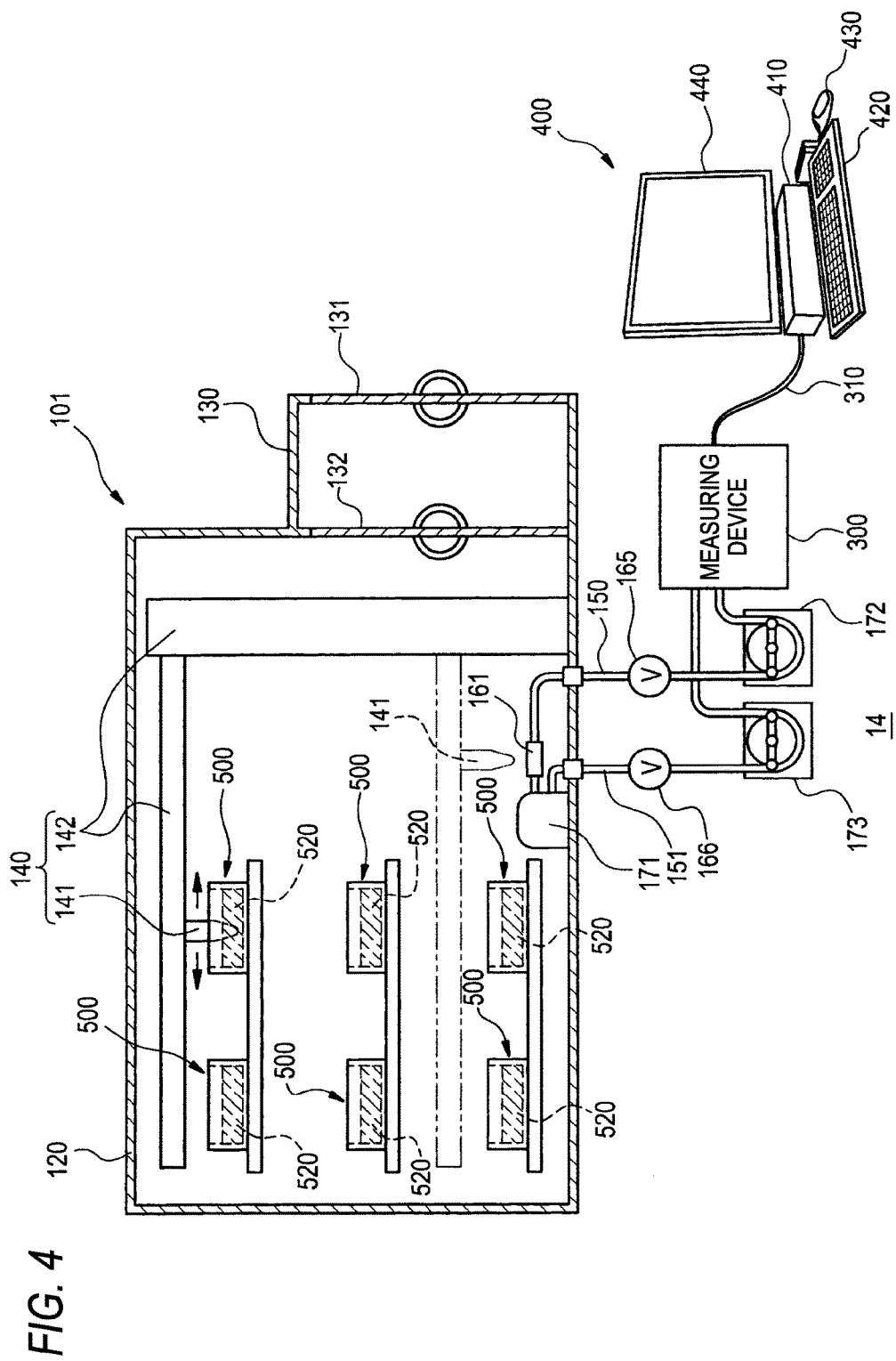
FIG. 4 is a schematic diagram of a cell culture apparatus 14 of a still further example of the embodiment of the invention.

FIG. 4 is a schematic diagram of a cell culture apparatus 14 of a still further example of the embodiment of the invention. In the cell culture apparatus 14 that will be described with reference to FIG. 4, components which are identical with those of the cell culture apparatuses 11 to 13 that have been described with reference to FIGS. 1 to 3 are denoted by the same reference numerals, and their description is omitted.

In the cell culture apparatus 14 of the example, the buffer substance supplier 171 disposed inside the sterile chamber 120, and the measuring device 300 disposed outside the sterile chamber 120 are connected to each other via a calibration flow path 151 in which the internal flow path is maintained to a sterile condition. From the buffer substance supplier 171 in the sterile chamber 120, therefore, the two flow paths, i.e., the delivery flow path 150 in which the ejection section 161 is disposed in the middle, and the calibration flow path 151 extend to the measuring device 300 disposed outside the sterile chamber 120, so that the buffer substance supplier 171 can supply the buffer substance to the measuring device 300 via each flow paths while maintaining a sterile condition (excepting contamination due to the sampling culture solution). Also in the calibration flow path 151, a one-way valve 166 and a peristalic pump 173 are disposed sequentially starting from the side which is closer to the sterile chamber 120. They are identical with the one-way valve 165 and peristalic pump 172 which are disposed in the delivery flow path 150, and hence their description is omitted.

When the calibration flow path 151 is disposed to enable the buffer substance to be supplied from the buffer substance supplier 171 to the measuring device 300, the substance can be used as a reference for improving or maintaining the measurement accuracy of the measuring device 300.

Figure 5:
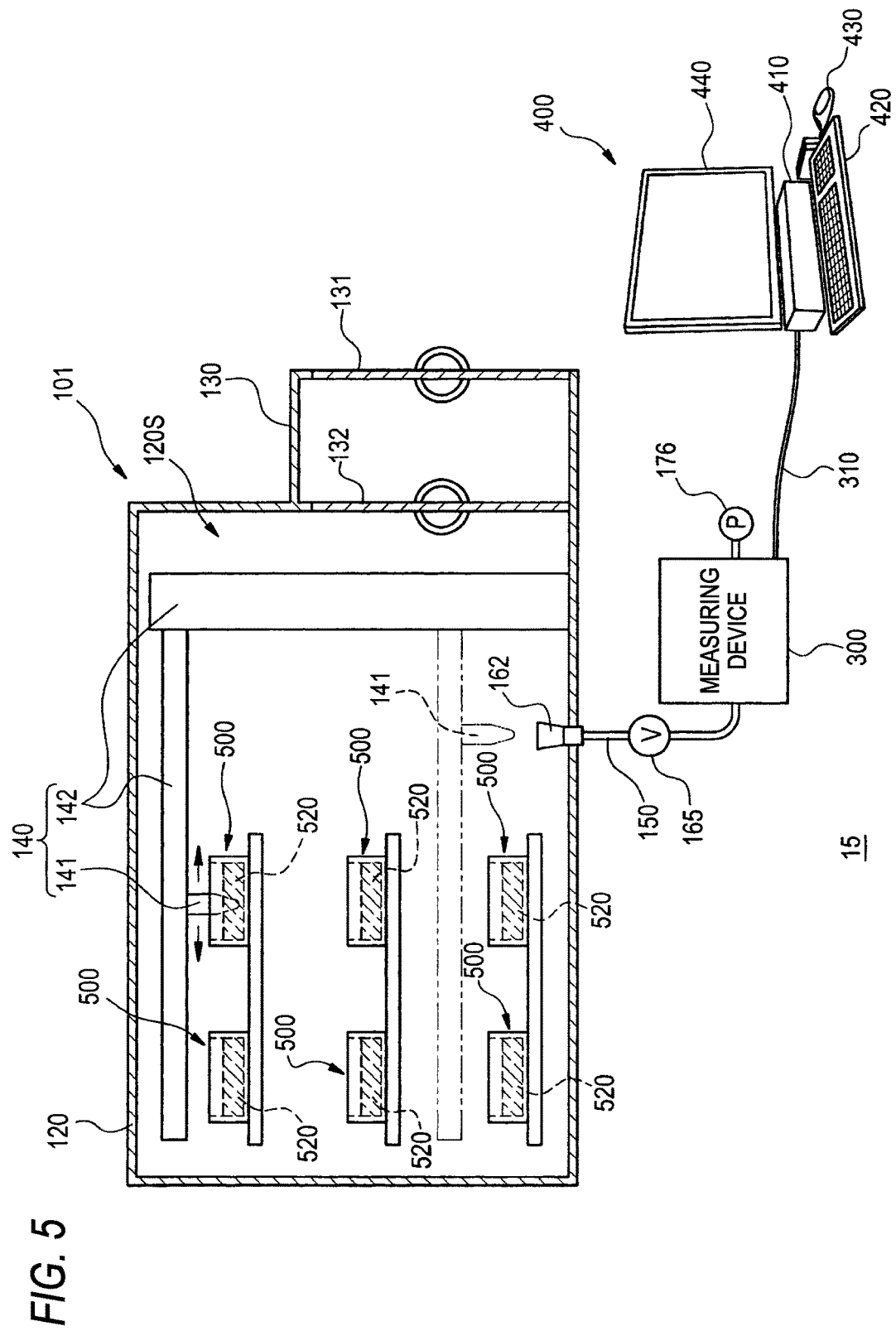
FIG. 5 is a schematic diagram of a cell culture apparatus 15 of a still further example of the embodiment of the invention.

FIG. 5 is a schematic diagram of a cell culture apparatus 15 of a still further example of the embodiment of the invention. In the cell culture apparatus 15 which will be described with reference to FIG. 5, components which are identical with those of the cell culture apparatuses 11 to 14 that have been described with reference to FIGS. 1 to 4 are denoted by the same reference numerals, and their description is omitted.

The cell culture apparatus 15 of the example includes an ejection section (sampling cup) 162, in place of the ejection section 161 and the buffer substance supplier 171 in the cell culture apparatus 11. In the delivery flow path 150, as shown in FIG. 5, the end portion on the side of the internal space of the sterile chamber 120 is connected to the ejection section 162. The cell culture apparatus 15 further includes a negative pressure pump 176 on place of the peristalic pump 172 in the cell culture apparatus 11. The end portion of the delivery flow path 150 on the side of the external space is connected to the negative pressure pump 176. The negative pressure pump 176 generates a negative pressure therein to suck the fluid in the delivery flow path 150.

In the cell culture apparatus 15, the injection port 141 ejects the sampling culture solution which is sucked from the cell incubator 500 that is to be sampled, to the ejection section 162. The sampling culture solution which is ejected to the ejection section 162 is sucked by the negative pressure pump 176 which is connected to the delivery flow path 150, to be sent to the measuring device 300, and then subjected to the measurement.

When the sampling of the culture solution 520 is performed, the negative pressure pump 176 may always suck the fluid in the delivery flow path 150. Alternatively, a configuration which detects the timing of the ejection of the sampling culture solution to the ejection section 162 may be disposed in the cell culture apparatus 15, and the suction may be performed only during a period from immediately before the timing to the delivery of the sampling culture solution to the measuring device 300.

As described above, also the cell culture apparatus 15 of the example can continuously perform sampling and measurement on the culture solution 520 in the cell incubator 500 which is accommodated in the sterile chamber 120, without, for example, taking out the cell incubator 500 to the outside of the sterile chamber 120 via the pass box 130. Therefore, the labor and time required in sampling can be remarkably reduced.

Also in the example, in the delivery flow path 150, the one-way valve 165 which does not interrupt the flow directed from the sterile chamber 120 toward the external space, and which interrupts that directed from the external space toward the sterile chamber 120 is disposed, and the peristalic pump 172 which sends the fluid in the delivery flow path 150 to the measuring device 300 is disposed. Therefore, the sampling culture solution ejected to the ejection section 162 is stably flown from the sterile chamber 120 toward the external space, and there is no possibility that the interior of the sterile chamber 120 is contaminated by the reverse flow.

In the cell culture apparatuses 11 to 15, the buffer substance supplier 171, the peristalic pump 172, the negative pressure pump 176, and the like constitute one configuration example of the culture solution delivering section in the invention. However, the configuration of the culture solution delivering section is not limited to this. In the cell culture apparatus 11, for example, the one-way valve 165 and the peristalic pump 172 may be disposed in the delivery flow path 150 which is inside the isolator 101.

In the cell culture apparatuses 11 to 15, the one-way valves 165, 166, the peristalic pumps 172, 173, the negative pressure pump 176, and the like may be disposed in the sterile chamber 120.

Although the invention has been described using the embodiments, the technical scope of the invention is not restricted to the scope of the description of the embodiments. It is obvious to those skilled in the art that various changes or improvements can be made on the embodiments.

According to an aspect of the invention, the culture solution in the cell incubator can be sampled without taking out the cell incubator via a pass box, and therefore the labor and time required in sampling can be remarkably reduced. Moreover, the flow in the delivery flow path through which the sterile space in the isolator communicates with the outside (non-sterile space) is limited to the direction that is directed from the inside of the sterile space toward the outside, and therefore contaminants which are produced in the non-sterile space do not enter the sterile space. In sampling or the like, consequently, the sterile space can be prevented from being contaminated, and hence it is possible to realize a secure cell culture environment.

What is claimed is:

1. A cell culture apparatus comprising:
    an isolator in which a sterile space accommodating a cell incubator filled with a culture solution containing cells to be cultured is disposed;
    a sampling unit configured to sample the culture solution in the cell incubator;
    a delivery flow path through which an inside of the sterile space and an outside of the sterile space communicate with each other, the delivery flow path configured to limit a flow in the delivery flow path to a direction that is directed from the inside of the sterile space toward the outside of the sterile space; and
    a culture solution delivering section configured to deliver the sampled culture solution to the outside of the sterile space via the delivery flow path.

2. The cell culture apparatus according to claim 1, wherein the delivery flow path includes a one-way valve which does not interrupt a flow directed from the inside of the sterile space toward the outside of the sterile space and which interrupts a flow directed from the outside of the sterile space toward the inside of the sterile space.

3. The cell culture apparatus according to claim 1, wherein the culture solution delivering section includes a buffer substance supplier configured to supply a buffer substance that is used when the sampled culture solution is delivered to the outside of the sterile space.

4. The cell culture apparatus according to claim 3, wherein the buffer substance supplier is disposed inside the sterile space, and is connected to an end portion of the delivery flow path on a side of the inside of the sterile space.

5. The cell culture apparatus according to claim 3, wherein the buffer substance supplier is disposed outside the sterile space, and is connected to the sterile space while maintaining a sterile condition.

6. The cell culture apparatus according to claim 1, wherein the culture solution delivering section includes a suction pump configured to suck the culture solution that is sampled by the sampling unit, toward a portion of the delivery flow path on a side of the outside of the sterile space.

7. The cell culture apparatus according to claim 6, wherein
    the suction pump is a peristalic pump which is disposed in the delivery flow path on a side of one of the inside and the outside of the sterile space.

8. The cell culture apparatus according to claim 6, wherein the suction pump is a negative pressure pump which is connected to an end portion of the delivery flow path on a side of the outside.

9. The cell culture apparatus according claim 1, wherein:
    the delivery flow path includes an ejection section which is disposed inside the sterile space; and
    the sampling unit is configured to suck a predetermined amount of the culture solution in the cell incubator and to eject the sucked culture solution into the ejection section.

10. The cell culture apparatus according to claim 1, further comprising a measuring device configured to perform measurement on the culture solution which is delivered to the outside of the sterile space via the delivery flow path.

11. The cell culture apparatus according to claim 10, further comprising a calibration flow path which is connected to the buffer substance supplier while maintaining a sterile condition, and through which the inside of the sterile space and outside of the sterile space communicate with each other, wherein
    the measuring device is configured to perform measurement on the buffer substance which is delivered to the outside of the sterile space via the calibration flow path.

* * * * *